United States Patent
Glace et al.

(10) Patent No.: US 10,238,521 B2
(45) Date of Patent: Mar. 26, 2019

(54) FLEX LOCK FOR ORTHOTIC BRACES

(71) Applicant: CORFLEX, INC., Manchester, NH (US)

(72) Inventors: Benjamin Glace, Dunbarton, NH (US); Steven Santaniello, Cranston, RI (US)

(73) Assignee: Corflex, Inc., Manchester, NH (US)

( * ) Notice: Subject to any disclaimer, the term of this patent is extended or adjusted under 35 U.S.C. 154(b) by 656 days.

(21) Appl. No.: 14/453,648

(22) Filed: Aug. 7, 2014

(65) Prior Publication Data
US 2015/0057586 A1    Feb. 26, 2015

Related U.S. Application Data

(60) Provisional application No. 61/869,235, filed on Aug. 23, 2013.

(51) Int. Cl.
*A61F 5/01*    (2006.01)

(52) U.S. Cl.
CPC .......... *A61F 5/0102* (2013.01); *A61F 5/0125* (2013.01); *A61F 2005/0167* (2013.01)

(58) Field of Classification Search
CPC ........ A61F 5/01; A61F 5/0102; A61F 5/0123; A61F 5/0125; A61F 2005/167; A61F 2005/0167
USPC ...................................... 602/16, 26
See application file for complete search history.

(56) References Cited

U.S. PATENT DOCUMENTS

| | | | | |
|---|---|---|---|---|
| 3,817,244 A * | 6/1974 | Taylor | A61F 5/0123 | 602/26 |
| 4,599,998 A * | 7/1986 | Castillo | A61F 5/0123 | 16/354 |
| 4,732,143 A * | 3/1988 | Kausek | A61F 5/0123 | 602/16 |
| 5,409,449 A * | 4/1995 | Nebolon | A61F 5/0125 | 16/333 |
| 5,443,444 A * | 8/1995 | Pruyssers | A61F 5/0123 | 602/16 |
| 5,460,599 A * | 10/1995 | Davis | A61F 5/0125 | 602/16 |
| 5,814,000 A * | 9/1998 | Kilbey | A61F 5/0125 | 602/16 |
| 7,037,287 B2 * | 5/2006 | Cormier | A61F 5/0125 | 602/16 |
| 7,189,212 B2 * | 3/2007 | Popp | A61F 5/0123 | 602/16 |
| 7,927,299 B2 * | 4/2011 | Krause | A61F 5/0123 | 602/16 |
| 2009/0137166 A1* | 5/2009 | Melius | A63B 31/11 | 441/64 |

(Continued)

*Primary Examiner* — Kari K Rodriquez
*Assistant Examiner* — Camtu T Nguyen
(74) *Attorney, Agent, or Firm* — Davis & Bujold, P.L.L.C.; Kimberly A. Peaslee

(57) ABSTRACT

A flex lock system for locking an orthotic brace having a push button for adjusting the range of flexion angles and a push button for adjusting the range of extension angles for the orthotic brace. The flex lock system has a tab having a receiving hole configured to fit around a push button and to prevent the push button from being depressed and adjusting the ranges of flexion or extension improperly. The flex lock system is made of a flexible material that has particular elasticity and compressibility to function as a flex lock as described.

5 Claims, 7 Drawing Sheets

(56) References Cited

U.S. PATENT DOCUMENTS

2011/0009786 A1* 1/2011 Chan .................. A61F 5/0125
602/16

\* cited by examiner

FLEX LOCK FOR ORTHOTIC BRACES

CROSS REFERENCE TO RELATED APPLICATIONS

This application claims the benefit of U.S. Provisional Application No. 61/869,235, filed Aug. 23, 2013, the content of which is incorporated by reference herein in its entirety.

FIELD OF THE INVENTION

The present invention relates to orthotic braces and more particularly to orthotic braces with flexible locking mechanisms.

BACKGROUND OF THE INVENTION

There are many forms of orthoses, or devices used externally to modify the structure and/or function of the skeletal and/or neuromuscular systems of the body. For example, there are orthoses that are applied to the neck, to the spine, to the upper limbs, and to the lower limbs. Additionally, there are many different purposes for using orthoses ranging from rehabilitative to prophylactic. Rehabilitation braces are typically used to limit the movement of a portion of the body following an injury or a surgery.

Certain rehabilitation braces, for example orthopedic knee braces, typically immobilize the leg and/or limit the motion in both the lateral and medial directions. These braces provide a mechanism to reduce the range of motion for a healing limb. The ability to limit flexion and extension are important features for an effective orthopedic knee brace. To maximize the benefits of an orthopedic brace it must be properly fitted and adjusted to the patient. Adjustment variables include fitting patients of various sizes and body proportions, and accommodating a variety of possible surgical sites. The adjustment of the brace will also be continual as the patient heals and can tolerate larger ranges of motion, as swelling is reduced, and the like. At times there may also be readjustment of the braces to adapt to accessories and/or product upgrades.

To accomplish the adjustability of the ranges for flexion and extension in existing orthotic braces, some brace designs utilize a system of holes in the hinge plate. For example, in U.S. Pat. No. 7,189,212 a series of holes incorporated into the brace's hinge plate is disclosed. This system of holes allows pin members to be adjusted into a small number of positions in the hinge plate to restrict the patient's range of movement during rehabilitation. The holes disclosed in the aforementioned patent are used with a pair of pins to limit extension and a pair of pins to limit flexion. The pins are retained on the hinge plate by strings and a retaining cover positioned over the hinge plate to prevent loss or unintended movement of the pins. The operator, or physician, must remove the retaining cover from the hinge plate to expose the pins for adjustment of the ranges. Once the pins are exposed, the operator must take out one or more of the four pins and place them into the most appropriate hole(s). Once this is done, the retaining cover must be placed back over the pins and latched closed so the retaining cover will stay in place and prevent the loss and/or movement of the pins.

Similarly, U.S. Pat. No. 5,443,444 discloses a system of holes in the hinge plate to accomplish the adjustability of the ranges for flexion and extension in an orthotic brace. This system of holes allows pin members to be adjusted into a small number of positions in the hinge plate to restrict the patient's range of movement during rehabilitation. The holes disclosed in the aforementioned patent are used with a pair of pins to limit extension and a pair of pins to limit flexion. The pins are retained on the hinge plate using tethers. The tethers are anchored to the hinge plate and a retaining cover is positioned over the hinge plate to prevent the loss and/or unintended movement of the pins. The operator, or physician, must move the retaining cover from the hinge plate to expose the pins for adjustment of the ranges. Once the pins are exposed, the operator must take out one or more of the four pins and place them into the most appropriate hole(s). Once this is done, the retaining cover must be placed back over the pins and latched closed so the retaining cover will stay in place and prevent the loss and/or movement of the pins.

These systems with hinge plates and removable pins are complicated to manufacture and are complicated to use. The removal of a retaining cover exposes the hinge plate and all the inner components of the brace to dust and other debris. Additionally, without the retaining cover the pins could be lost or could inadvertently move, which could cause the patient to be re-injured when they suddenly experience a wider range of motion than is appropriate for their stage in the healing process. In contrast, the flex lock for orthotic braces of the present invention is a cost effective and easy to use mechanism for locking the flexion and extension limits on an orthotic brace.

Other existing orthotic braces accomplish the adjustability of the ranges for flexion and extension by using screws or buttons to adjust and lock the brace in position. For example, PCT Appln. No.: PCT/US84/00336 discloses a single cam-slot mechanism including flexible plungers for simulating the flexural motion of the wearer's limb and a lock for limiting that range of motion. This system includes two set screws, which must be adjusted with a screwdriver to raise and/or lower a set of springs that are in contact with a moveable cam in a slot designed to simulate a patient's range of motion. By turning the set screws, the springs are "set" and the cam in the slot can only move up until the cam meets the springs, thus limiting only the range of motion for flexion.

Similarly, In U.S. Pat. No. 8,425,439 a lock is disclosed for an orthotic brace. The orthotic brace in the aforementioned patent is configured to either 1) move freely with no limit either on flexion or extension or 2) to be locked in a desired fixed position or angle. The lock is comprised of a push-in and turn type of lock that fixes the orthotic brace in a static position. In contrast, the flex lock for an orthotic brace of the present invention allows for quick and easy movement and locking of the brace to control the ranges for both flexion and extension to allow a patient to experience the proper range of motion, which can be adjusted easily by the patient as the patient heals. The flex lock for an orthotic brace of the present invention does not require additional tools (e.g. screwdriver, wire cutters, etc.) or removable parts (e.g. pins, wires, etc.). Furthermore, the flex lock of the present invention provides a mechanism for locking the preferred ranges for flexion and extension.

Other existing orthotic braces accomplish the adjustability of the ranges for flexion and extension by using outwardly biased push buttons that require an external part to "lock" each button in place, once set. See, for example, in U.S. Pat. No. 7,833,181 two buttons are capable of adjusting the flexion and the extension ranges, respectively, but the use of buttons containing holes near the outer ends thereof is required. This system requires a physician or technical assistant to thread a wire or a plastic tie through each of the openings of the buttons to discourage re-setting or tampering with the angular ranges of the brace. Locking or zip ties can also be used. This system is not only cumbersome, but the twisted wire and/or ties can cause scrapes or other injuries to the patient as the ends stick out from the outer surface of the brace hinge. In addition, the mechanism requires the ties to be cut off before the button can be moved. Once the button is moved into the next setting, as the patient is progressing in treatment, another zip tie or wire must be re-threaded through the hole in the push button and twisted to lock the button in place. This is unnecessarily difficult for the patient, but is needed with this system in order to prevent inadvertent re-setting of the brace's angular settings, which could reinjure the patient as discussed above.

One aspect of the present invention is a flexible locking mechanism for use on an orthotic brace. The present invention improves the usability of orthotic braces by providing the user with secure locking mechanism for the angular ranges for both flexion and extension without the need for any tools or any risk of losing components of the brace as in existing orthotic braces. Additionally, the present invention provides a mechanism that ensures that there will not be any inadvertent re-setting of the angular settings, which could re-injure a patient.

SUMMARY OF THE INVENTION

It has been recognized that there is a need for orthotic braces with locking mechanisms for use in setting the angular flexion and extension ranges for patients that are secure, easy to use, and do not require any particular expertise or tooling.

One aspect of the present invention is a flex lock system for orthotic braces, comprising: a hinge for an orthotic brace having a center region and an outer edge; a push button for adjusting the range of flexion for the orthotic brace, positioned on the outer edge of the hinge; a push button for adjusting the range of extension for the orthotic brace, positioned on the outer edge of the hinge; a tab having a first end, a second end, and a center region wherein the center region of the tab is affixed to the center region of the hinge either directly or indirectly; a pair of receiving holes positioned at the first end and the second end of the tab; and a pair of pull tabs positioned at the outermost portion of the first end and the second end of the tab.

One embodiment of the flex lock system is wherein the tab comprises an elastomeric material.

Another aspect of the present invention is flex lock system for orthotic braces, comprising: a hinge for an orthotic brace having a center region and an outer edge; a push button for adjusting the range of flexion for the orthotic brace, positioned on the outer edge of the hinge; a push button for adjusting the range of extension for the orthotic brace, positioned on the outer edge of the hinge; a pair of tabs having a first end and a second end, wherein the second end is affixed to the center region of the hinge either directly or indirectly; a receiving hole positioned at the first end of the tab; and a pull tab positioned at the outermost portion of the first end of the tab.

One embodiment of the flex lock system is wherein the tab comprises an elastomeric material.

Another aspect of the present invention is a flex lock, comprising a tab having a first end, a second end, and a center region; a pair of receiving holes positioned at the first and second ends of the tab, wherein the receiving holes are configured to fit over a push button on an orthotic brace; and a pair of pull tabs positioned at the outermost portion of the first and second ends of the tab, wherein the tab is configured to be attached either directly or indirectly to a hinge on an orthotic brace.

One embodiment of the flex lock is wherein the tab comprises an elastomeric material.

These aspects of the invention are not meant to be exclusive and other features, aspects, and advantages of the present invention will be readily apparent to those of ordinary skill in the art when read in conjunction with the following description, appended claims, and accompanying drawings.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A flex lock system for locking an orthotic brace will be described. The flex lock system is configured to be used with the hinge of an orthotic brace having a push button for adjusting the range of flexion angles and a push button for adjusting the range of extension angles for the orthotic brace. The push buttons are biased outward and are depressed to move and to set the extension and flexion ranges suitable for the particular patient at the particular time in their healing process. The flex lock system has a tab or a pair of tabs having a receiving hole configured to fit around the push button and to prevent the push button from being depressed and adjusting the ranges of flexion or extension when not appropriate. The flex lock system is made of a flexible material that has particular elasticity and compressibility to function as a flex lock as described herein.

Figure 1:
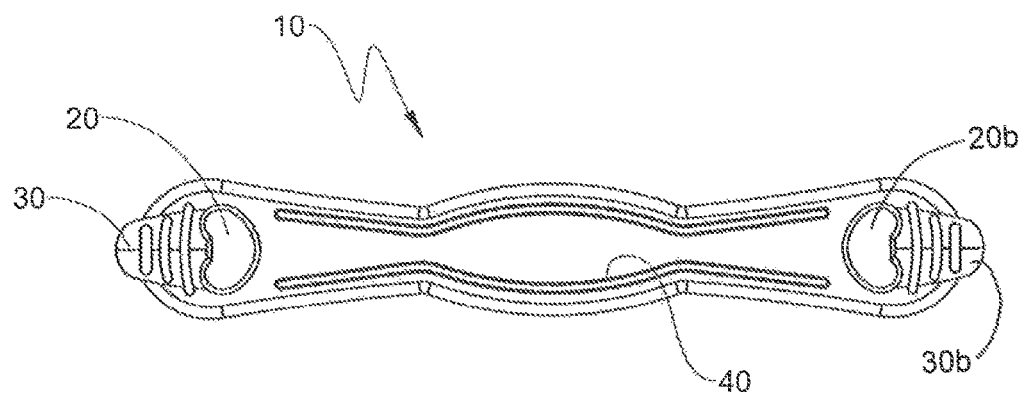
FIG. 1 shows a top view of one embodiment of a flex lock for an orthotic brace of the present invention.
Figure 8:
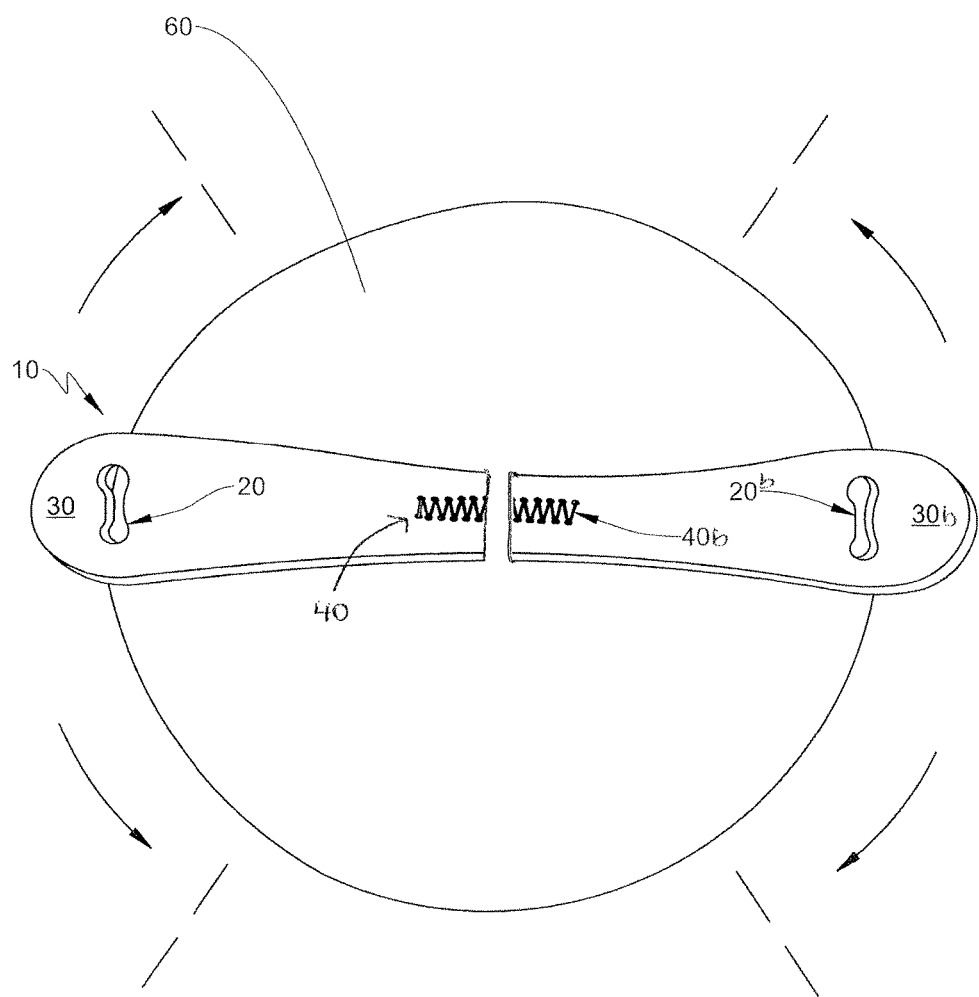
FIG. 8 shows a top view of a pad for a hinge for an orthotic brace with a second embodiment of the flex lock of the present invention affixed to the pad.

Referring to FIG. 1, a top view of one embodiment of a flex lock for an orthotic brace of the present invention is shown. More particularly, one embodiment of the flex lock 10 is shown with two receiving holes 20, 20b on either end of a tab. The outermost ends of the flex lock comprise pull tabs 30, 30*b*. In certain embodiments, the flex lock is configured to be fastened to the orthotic brace's hinge in such a way as to lock both the flexion and the extension buttons using a connection area 40 and a flex lock with a pair of receiving holes 20, 20*b* and pull tabs 30, 30*b*. In certain other embodiments, as shown in FIG. 8, the flex lock can be configured to have two separate portions, each fastened to the orthotic brace's hinge and responsible for locking either the extension or the flexion button, where each portion has a single receiving hole and a single pull tab.

Figure 2:
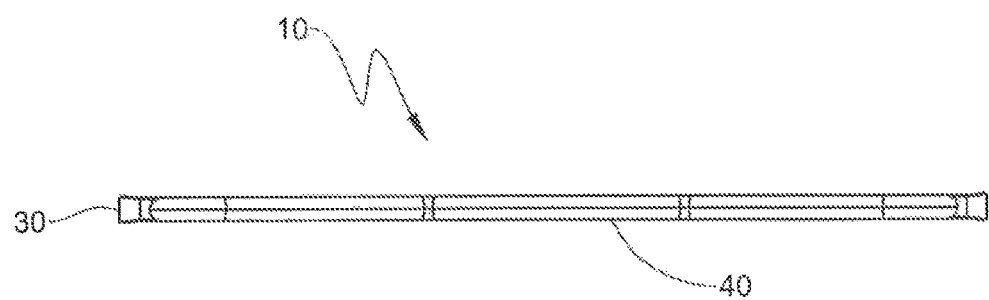
FIG. 2 shows a side view of one embodiment of a flex lock for an orthotic brace of the present invention.

Referring to FIG. 2, a side view of one embodiment of a flex lock for an orthotic brace of the present invention is shown. Here, the flex lock is shown as one thickness throughout. In certain embodiments, the flex lock may be of varying thicknesses along the length of the tab. In certain embodiments, the center region 40 may be thicker or thinner. In certain embodiments, the pull tabs or outermost portion of the tab 30 may be thicker or thinner.

In one embodiment of the flex lock of the present invention, the flex lock is affixed to the center region of the hinge directly. In one embodiment of the flex lock of the present invention, the flex lock is affixed to the center region of the hinge indirectly. In certain embodiments, the flex lock is affixed to a pad, which is held in place on the orthotic brace using Velcro hook and loop or some other mechanism. In certain embodiments, the pad is removable. In certain embodiments, the flex lock is grommeted, sewn, or otherwise permanently affixed to the pad.

In certain embodiments, the flex lock may be comprised of two separate tabs. A pair of tabs may be used to lock the push buttons of the orthotic brace. In certain embodiments, each of the flex locks would be a different color representing flexion or extension. In certain embodiments, the flex locks are affixed to the center region of the hinge directly. In one embodiment of the flex lock of the present invention, the flex locks are affixed to the center region of the hinge indirectly. In certain embodiments, the flex locks are affixed to a pad, which is held in place on the orthotic brace using Velcro hook and loop or some other mechanism. In certain embodiments, the pad is removable. In certain embodiments, the flex locks are grommeted, sewn, or otherwise permanently affixed to the pad.

Figure 3:
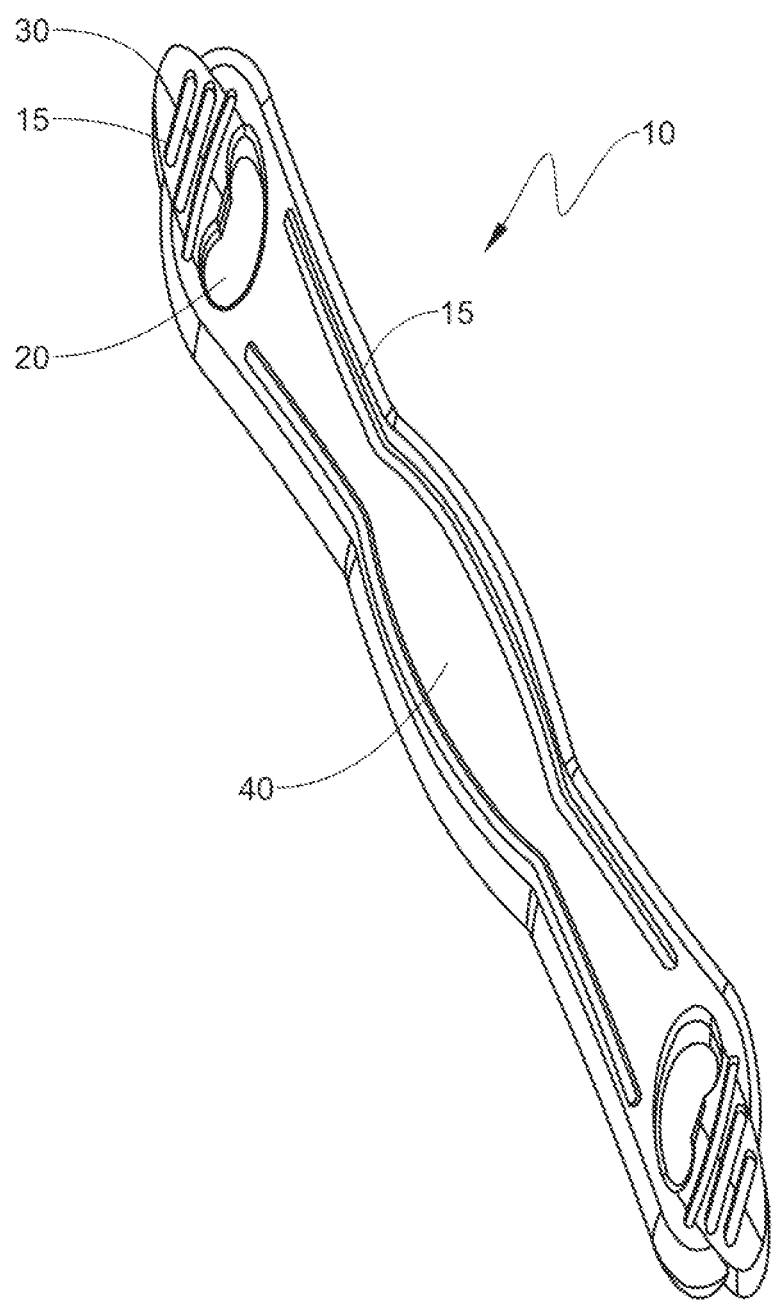
FIG. 3 shows a perspective view of one embodiment of a flex lock for an orthotic brace of the present invention.

Referring to FIG. 3, a perspective view of one embodiment of a flex lock for an orthotic brace of the present invention is shown. In certain embodiments, the flex lock could have areas of varying thickness 15 that add strength to the tab and withstand repeated stretching for materials used in the flexible locking system. In certain embodiments, the flex lock is die cut. In certain embodiments, the flex lock is stamped. It is understood that many suitable materials and methods of manufacture known to those of skill in the art could be used to produce the flex lock of the present invention. In certain embodiments, the flex lock is compression molded. In certain embodiments, the flex lock is injection molded.

Figure 4:
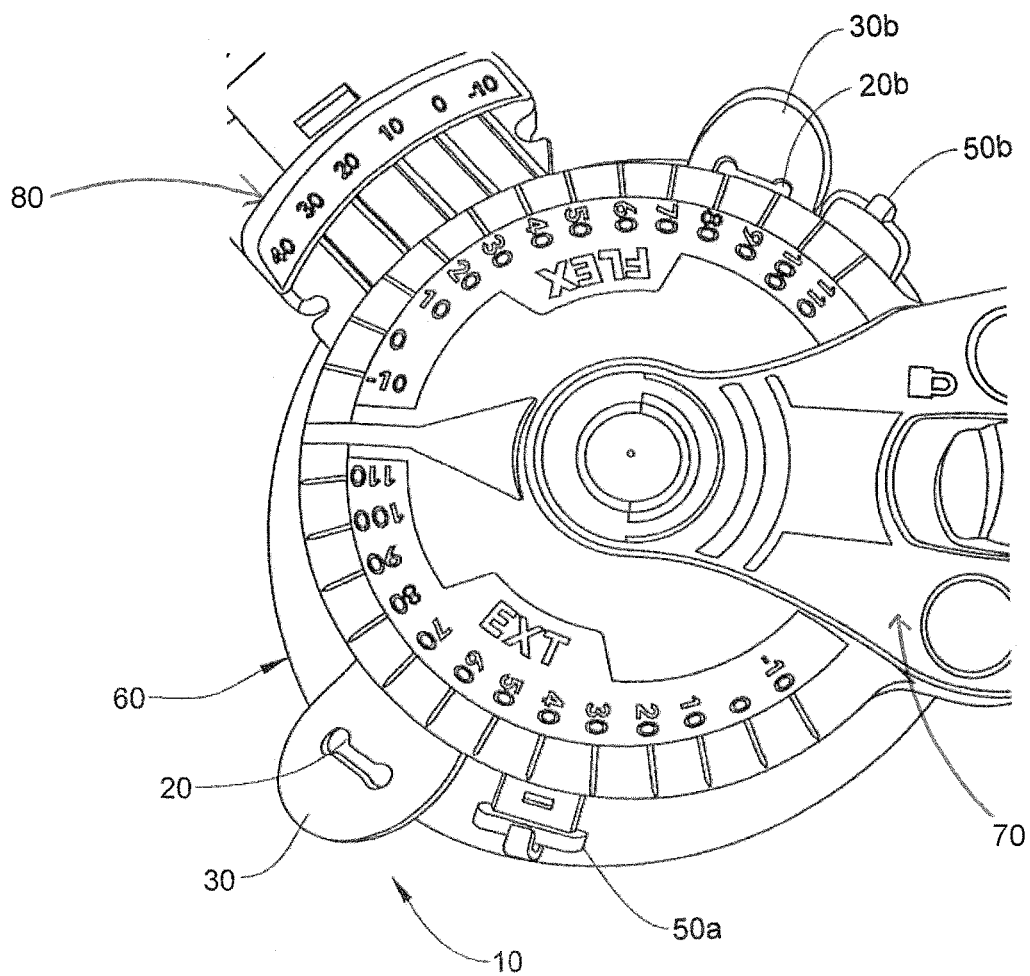
FIG. 4 shows a top view of a hinge for an orthotic brace with one embodiment of the flex lock of the present invention in the unlocked position.

Referring to FIG. 4, a top view of a hinge for an orthotic brace with one embodiment of the flex lock of the present invention in the unlocked position is shown. More particularly, a hinge for an orthotic brace is shown with two push buttons 50*a*, 50*b* used for adjusting the ranges for the flexion and extension angles for a patient at a given time during treatment. A fixed upper strut 70 is formed integrally with the circular hinge, while flexion and extension is possible by moving a rotatably connected lower strut 80. Also, a removable pad 60 is shown underneath the hinge plate which adds comfort to the brace when worn by a patient. Also shown are the ends of one embodiment of the flex lock of the present invention 10. The ends contain receiving holes 20, 20*b* for use in wrapping around the push buttons 50*a*, 50*b* to stabilize the push buttons. The material for the tabs should be such that it is flexible enough to extend around the push button, but not so flexible, or compressible, as to allow the push button to be depressed, and therefore capable of moving to another non-preferred angular setting. In certain embodiments, the tabs have a pull tab region 30, 30*b* which facilitates the use of the tab to aid in stretching the tab around the push button. Here, both of the ends of the flex lock are in the unlock orientation (i.e. they are not on or around the push buttons).

Figure 5:
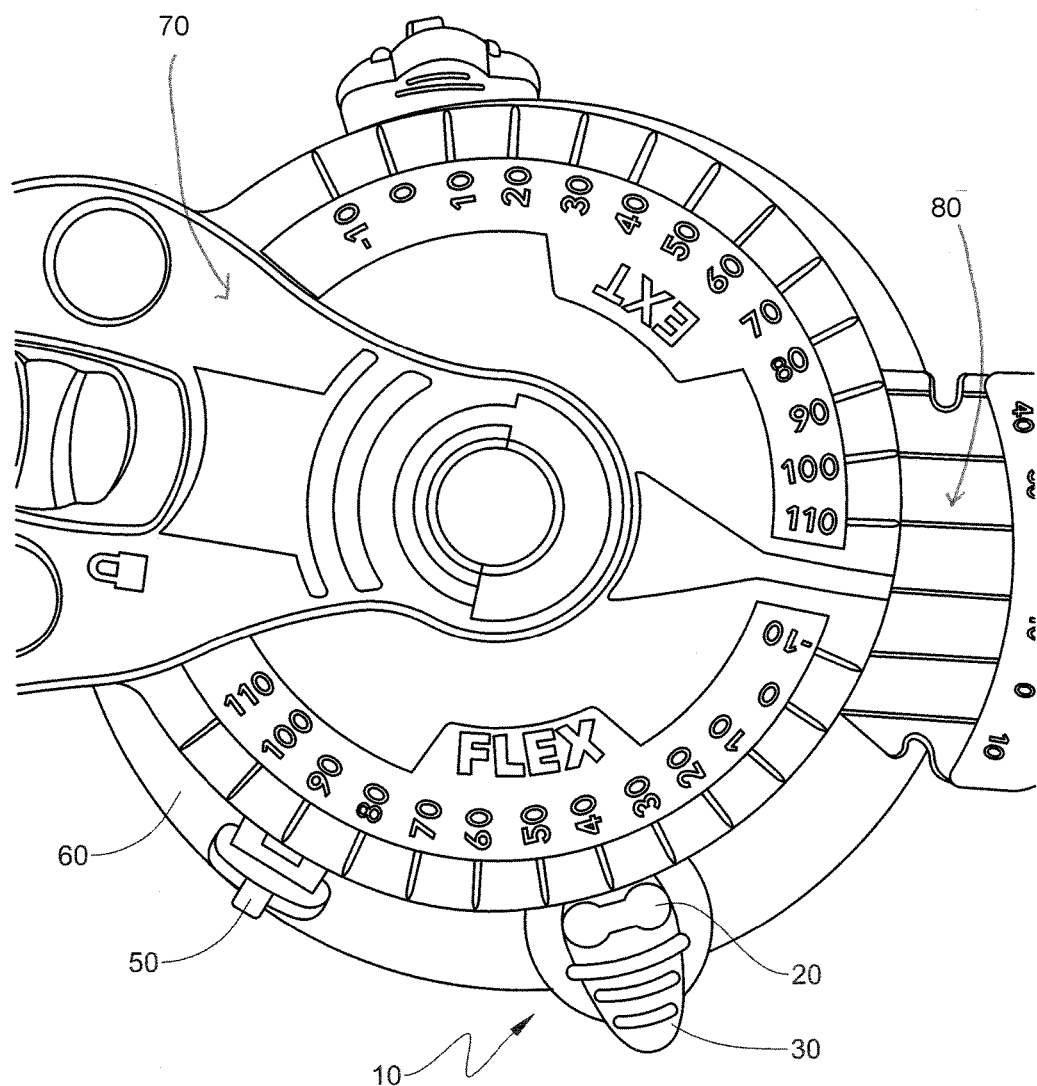
FIG. 5 shows a top view of a hinge for an orthotic brace with one embodiment of the flex lock of the present invention in the partially unlocked position.

Referring to FIG. 5, a top view of a hinge for an orthotic brace with one embodiment of the flex lock of the present invention in the partially unlocked position is shown. More particularly, a hinge for an orthotic brace is shown with two push buttons 50 used for adjusting the ranges for the flexion and extension angles for a patient via the rotatably connected lower strut 80 at a given time during treatment. Also, a removable pad 60 is shown underneath the hinge plate which adds comfort to the brace when worn by a patient. Also shown are the ends of one embodiment of the flex lock of the present invention 10. The ends contain receiving holes 20 for use in wrapping around, or receiving, the push buttons 50 to stabilize the push buttons. Here, the end of the flex lock on the flexion side of the hinge is in the unlock orientation (i.e. it is not on or around the push button), but the end of the flex lock on the extension side of the hinge is shown on or around the push button and is therefore in the locked position. The ranges of motion in flexion and extension are possible because an upper strut 70 is in a fixed position, while the lower strut 80 of the orthotic brace rotates about the center of the circular hinge and is blocked by the placement of a push button 50.

Figure 6:
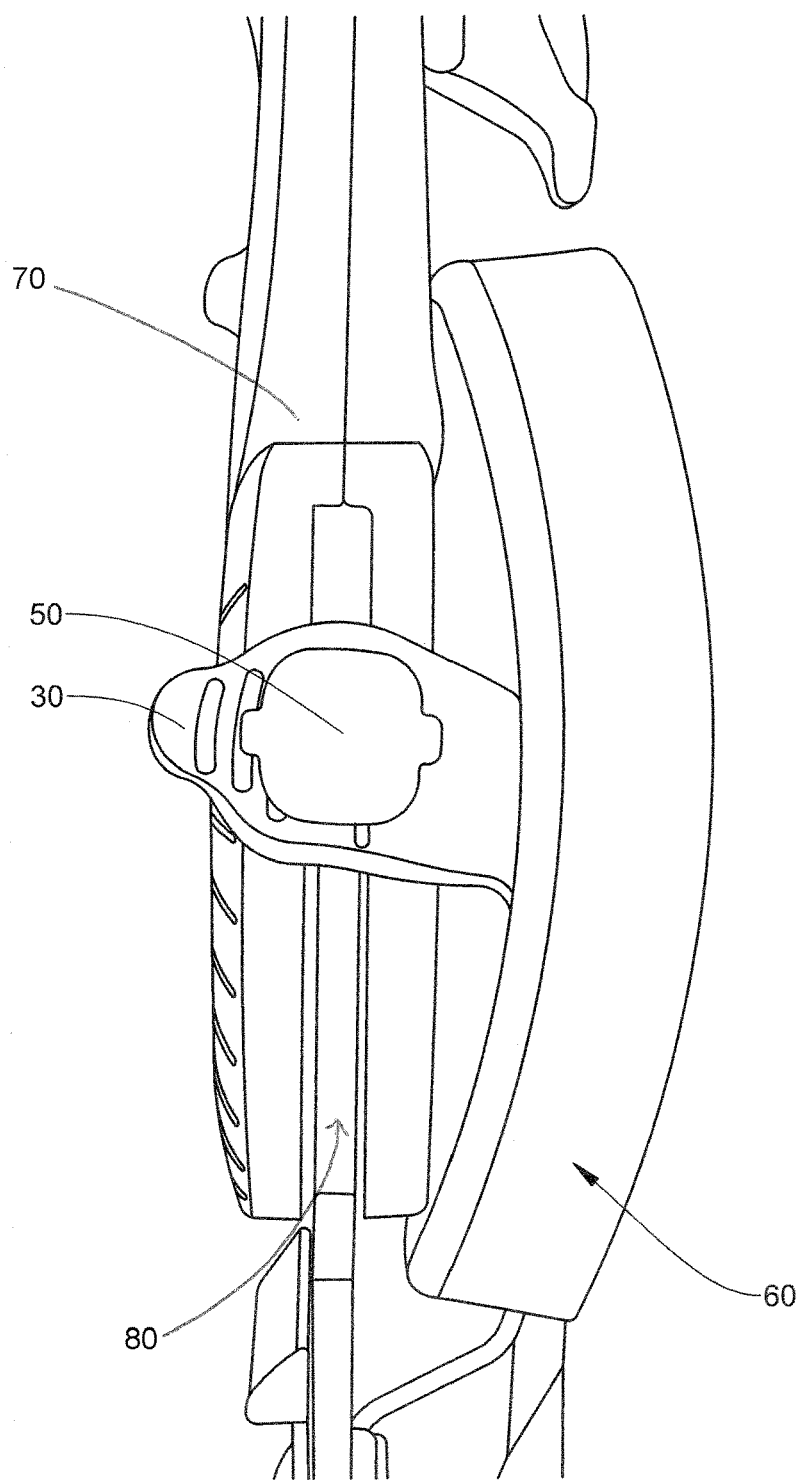
FIG. 6 shows a side view of a hinge for an orthotic brace with one embodiment of the flex lock of the present invention in the locked position.

Referring to FIG. 6, a side view of a hinge for an orthotic brace with one embodiment of the flex lock of the present invention in the locked position is shown. More particularly, the push button 50 is shown inside the receiving hole of the flex lock The outermost portion of the end of the flex lock is shown with a pull tab 30 for use in locking and unlocking the push button used to adjust one of the angular ranges on the orthotic hinge. Also shown is the pad 60 on the underside of the hinge for the orthotic brace, which provides added comfort to the patient when they are wearing the brace. It is possible to see that the upper strut 70 is integrally formed with the circular hinge, while the lower strut 80 is received within the circular hinge and rotates about the center of the circular hinge to provide for ranges of angular motion.

Figure 7:
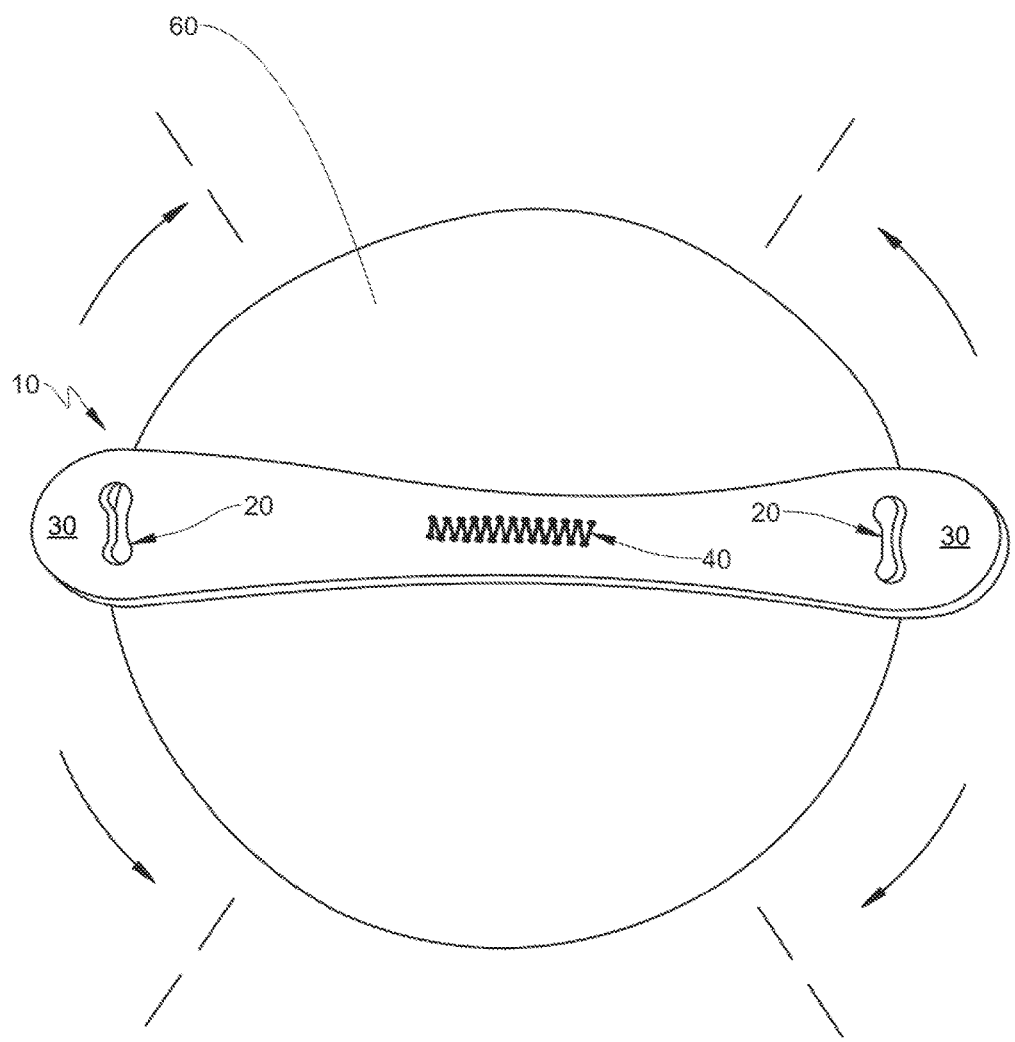
FIG. 7 shows a top view of a pad for a hinge for an orthotic brace with one embodiment of the flex lock of the present invention affixed to the pad.

Referring to FIG. 7, a top view of a removable pad for a hinge for an orthotic brace with one embodiment of the flex lock of the present invention affixed to the pad is shown. Here, one embodiment of the flex lock 10 of the present invention is shown where there is one tab with a pair of receiving holes 20. The tab is secured to a removable pad 60 by sewing. It is understood that any method of attachment known to those of skill in the art could be used. Also shown here is a representation of the flexibility present in the tab (denoted with dashed lines and arrows) such that one tab may be used to capture and secure two push buttons located on either side of a hinge for an orthotic brace along the range of angular settings needed for both flexion and extension management. It is understood that two separate tabs could also be used—one for each push button—as shown in FIG. 8.

The flex lock system is made of a flexible material that has particular elasticity and compressibility to function as a flex lock as described herein. In certain embodiments, the flex lock comprises silicon. In certain embodiments, the flex lock comprises urethane. In certain embodiments, the flex lock comprises neoprene, buna-N, rubber, or the like. In certain embodiments, the flex lock comprises fabric, plastic or other material.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed:

1. A flex lock system for orthotic braces, comprising:
a circular hinge for an orthotic brace having a center region, a front face, and an outer circumference;
an upper strut of the orthotic brace being integrally formed with the circular hinge;
a lower strut of the orthotic brace being rotatably connected to the center region of the circular hinge to provide for flexion and extension ranges of motion about the circular hinge when the brace is worn by a user;
a first push button for adjusting the range of flexion for the orthotic brace via the lower strut, where the first push button is positioned on the outer circumference of the circular hinge in a direction perpendicular to the front face of the circular hinge;
a second push button for adjusting the range of extension for the orthotic brace via the lower strut, where the second push button is positioned on the outer circumference of the circular hinge in a direction perpendicular to the front face of the circular hinge;
a flex lock having a first end, a second end, and a center region wherein the center region of the flex lock is affixed to the center region of the circular hinge either directly or indirectly;
a first receiving hole positioned at the first end of the flex lock and a second receiving hole positioned at the second end of the flex lock, wherein when the first and second push buttons are received in a respective first and second receiving hole the rotatable adjustment of the lower strut is prevented; and
a first pull tab positioned at the first end of the flex lock to facilitate an association and a disassociation of the first push button with the first receiving hole and a second pull tab positioned at the second end of the flex lock to facilitate an association and a disassociation of the second push button with the second receiving hole.

2. The flex lock system of claim 1, wherein the flex lock comprises an elastomeric material.

3. The flex lock system of claim 1, wherein the flex lock comprises two separate portions each having a first end and a second end;
the first ends of each of the two separate portions being attached to the center region of the circular hinge; and
the second ends of each of the two separate portions each comprising a pull tab and a receiving hole for locking the orthotic brace in various flexion and extension positions.

4. A flex lock system for orthotic braces, comprising:
a circular hinge for an orthotic brace having a center region, a front face, and an outer circumference;
an upper strut of the orthotic brace being integrally formed with the circular hinge;
a lower strut of the orthotic brace being rotatably connected to the center region of the circular hinge to provide for flexion and extension ranges of motion about the circular hinge when the brace is worn by a user;
a first push button for adjusting the range of flexion for the orthotic brace via the lower strut, where the first push button is positioned on the outer circumference of the hinge in a direction perpendicular to the front face of the circular hinge;
a second push button for adjusting the range of extension for the orthotic brace via the lower strut, where the second push button is positioned on the outer circumference of the hinge in a direction perpendicular to the front face of the circular hinge; and
a flex lock comprising:
a first portion of the flex lock having a first end and a second end, wherein the second end is affixed to the center region of the circular hinge either directly or indirectly;
a second portion of the flex lock having a first end and a second end, wherein the second end is affixed to the center region of the circular hinge either directly or indirectly;
a first receiving hole positioned at the first end of the first portion of the flex lock, wherein when the first push button is received in the first receiving hole the adjustment of the lower strut in the flexion range of motion is prevented;
a second receiving hole positioned at the first end of the second portion of the flex lock, wherein when the second push button is received in the second receiving hole the adjustment of the lower strut in the extension range of motion is prevented;
a first pull tab positioned at the first end of the first portion of the flex lock to facilitate an association and a disassociation of the first push button with the first receiving hole; and
a second pull tab positioned at the first end of the second portion of the flex lock to facilitate an association and a disassociation of the second push button with the second receiving hole.

5. The flex lock system of claim 4, wherein the first and the second flex lock portions comprise an elastomeric material.

* * * * *